United States Patent
Cheminal et al.

(10) Patent No.: US 6,395,941 B1
(45) Date of Patent: *May 28, 2002

(54) PROCESS FOR THE PURIFICATION OF 1,1, 1,2-TETRAFLUOROETHANE

(75) Inventors: Bernard Cheminal, Brignais; Andre Lantz, Vernaison, both of (FR)

(73) Assignee: Elf Atochem, S.A., Puteaux (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/888,294

(22) Filed: Jul. 3, 1997

Related U.S. Application Data

(63) Continuation of application No. 08/600,087, filed on Feb. 12, 1996, now abandoned, which is a continuation of application No. 08/307,091, filed on Sep. 16, 1994, now abandoned, which is a continuation of application No. 08/086,063, filed on Jul. 6, 1993, now abandoned.

(30) Foreign Application Priority Data

Aug. 5, 1992 (FR) .............................................. 92 09700

(51) Int. Cl.$^7$ ............................................... C07C 17/08
(52) U.S. Cl. ........................................ 570/169; 570/177
(58) Field of Search .................................. 570/169, 177

(56) References Cited

U.S. PATENT DOCUMENTS

| | | | | |
|---|---|---|---|---|
| 4,158,675 A | * | 6/1979 | Potter .......................... | 570/169 |
| 5,430,205 A | * | 7/1995 | Cheminal et al. ............ | 570/177 |
| 5,705,718 A | * | 1/1998 | Cheminal et al. ............ | 570/177 |

FOREIGN PATENT DOCUMENTS

| EP | 446869 A1 | 3/1991 |
|---|---|---|
| EP | 449614 A2 | 3/1991 |
| EP | 449617 A2 | 3/1991 |
| EP | 0 548 742 | 6/1993 |
| JP | 43-10601 | 5/1968 |
| JP | 56-038131 | 9/1981 |
| JP | 62-023728 | 5/1987 |

* cited by examiner

*Primary Examiner*—Alan Siegel
(74) *Attorney, Agent, or Firm*—Smith, Gambrell & Russell, LLP

(57) ABSTRACT

In order to remove the impurities (in particular 1-chloro-2, 2-difluoroethylene) present in crude 1,1,1,2-tetrafluoroethane (F134a), a gaseous mixture of crude F134a and hydrofluoric acid is treated in the gas phase, in the presence of a fluorination catalyst, at a temperature of between 200 and 380° C. and under a pressure between atmospheric pressure and 2.5 MPa, the HF/F134a molar ratio being between 0.05 and 0.5.

17 Claims, No Drawings

PROCESS FOR THE PURIFICATION OF 1,1,1,2-TETRAFLUOROETHANE

This is a continuation of application Ser. No. 08/600,087, filed Feb. 12, 1996, which is a continuation of U.S. Ser. No. 08/307,091 filed Sep. 16, 1994, now abandoned; which is a continuation of U.S. Ser. No. 08/086,063 filed Jul. 6, 1993, now abandoned.

FIELD OF THE INVENTION

The present invention relates to the field of fluorinated hydrocarbons and, more particularly, has as its subject the purification of 1,1,1,2-tetrafluoroethane.

BACKGROUND OF THE INVENTION

This compound, known in the profession under the name F134a, is especially intended to replace dichlorodifluoromethane (F12) currently used as a refrigerating fluid but suspected of contributing to the depletion of the stratospheric ozone layer. In order to do this, F134a must satisfy quality standards with respect to the presence of a priori toxic impurities, such as chlorofluorinated olefins. These include in particular 1-chloro-2,2-difluoroethylene (F1122) which, given its boiling point (−17.7° C.), proves to be very difficult to completely remove from F134a (B.p.=−26.5° C.) by simple distillation, especially under pressure.

Now, one of the industrial syntheses of F134a consists of a gas phase catalytic fluorination of 1-chloro-2,2,2-trifluoroethane (F133a) which always produces variable quantities of F1122 as a by-product by a dehydrofluorination side reaction.

In order to solve this problem, various techniques have already been proposed. Thus, the U.S. Pat. No. 4,158,675 describes a process for in-line treatment consisting in reacting the gases resulting from the main reaction:

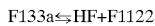

in a second reactor maintained at a lower temperature than that of the main reaction. From a gas mixture whose F1122 content, relative to the organic compounds, is 5300 vpm (volume per million), the in-line treatment at 160° C. leads to a F1122 value of 7 vpm. The major disadvantage of this process lies in the necessity of treating a significant gas flow rate and thus having a high reaction volume, which leads to a prohibitive investment and a prohibitive maintenance cost. Moreover, the lifetime of the catalyst (bulk chromium oxide) is not mentioned and, to compensate for the loss in catalytic activity, it may prove to be necessary to progressively increase the temperature, which may have inter alia the immediate consequence of a partial retrogradation of F134a to F133a by reaction with HCl. Moreover, the presence of HCl in the gases also risks causing a corrosion problem.

The patent application EP 0,467,531 describes a process for distilling azeotropic HF/F134a/F1122 mixtures. The complexity of this process and the high energy consumption which it requires do not make it particularly attractive.

Another technique, described in the patent application EP 0,446,869, consists in carrying out the synthesis of F134a from trichloroethylene and HF in the gas phase in two reactors arranged in series. In the first, F133a is converted at high temperature to F134a accompanied by F1122; the flow leaving this first reactor, to which trichloroethylene is added, passes through a second catalytic reactor at a lower temperature in order to convert the trichloroethylene and F1122 to F133a. The major disadvantage of such a process lies in the low productivity of the second reactor, limited by the removal of the heat produced by the reaction, on the one hand, and by the obligation to work with a high contact time in order to achieve very low F1122 values, on the other hand. Another disadvantage of this technique lies in the risk of retrogradation of F134a to F133a in the presence of HCl as soon as the temperature is raised too high. This obligation to perfectly control the temperature then leads to a risk of the appearance of unconverted F1122 since the equilibrated reaction:

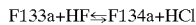

depends not only on the HF/F1122 and F133a/F1122 molar ratios but also on the temperature and the pressure. In this respect, there may be mentioned the patent EP 36123 relating to the catalytic addition of HF to (chloro)fluorinated olefins, especially pure F1122 (Example 4), whose fluorination at a controlled temperature (120 to 131° C.) allows unconverted F1122 to remain at the reactor outlet.

As other means of removing olefins, there may be mentioned:

Catalytic hydrogenation (patent application WO 90/08750): this method requires expensive catalysts (precious metals) and leads to hydrogenated saturated compounds other than F133a which have to be separated subsequently; moreover, the hydrogen always entrains a small amount of F134a by vapor pressure.

Physical adsorption on a mixture of oxides of manganese and of copper (hopcalite): the major disadvantage of this process, described in the patent application EP 370,688, lies in the requirement to regularly regenerate this solid adsorbent after use; this leads to losses of F134a by more or less selective adsorption and a significant concentration of olefin during the regeneration cycle.

Extractive distillation (patent application EP 472,391) of F134a/F1122 mixtures using suitable solvents (trichloroethylene, perchloroethylene, and the like): the main disadvantage of this technique lies in the complexity of the equipment (additional distillation columns to recycle the purified solvent), the high effect of the energy cost (successive evaporations) and the more or less efficient yield of the processing.

To avoid the disadvantages of the abovementioned techniques, the present invention provides a particularly effective and economic means for purifying crude F134a containing unsaturated impurities.

DESCRIPTION OF THE INVENTION

The process according to the invention consists in treating a gaseous mixture of crude F134a and HF in the gas phase, in the absence of hydrochloric acid, at a temperature of between 200 and 380° C. and under a pressure ranging from atmospheric pressure to 2.5 MPa, in the presence of a fluorination catalyst, the HF/F134a molar ratio being between 0.05 and 0.5.

EXAMPLES

During this treatment, hydrofluoric acid is added to the (chloro)fluorinated olefins, such as F1122, 1,2,2-trifluoroethylene (F1123) and 1,1,1,4,4,4-hexafluorobutene (CF$_3$CH=CHCF$_3$), and converts them to saturated compounds which are easy to separate and/or recycle by distillation.

In crude F134a, the level of olefinic impurities can vary between 100 and 10,000 ppm (0.01 to 1%) with respect to F134a and is most often between 500 and 5,000 ppm (0.05 to 0.5%). Besides (chloro)fluorinated olefins, crude F134a can also contain variable quantities of other compounds such as, for example, F133a (0 to 7%), 1,1,1-trifluoroethane (F143a) and pentafluoroethane (F125). The presence of these saturated impurities does not harm the efficiency of the process according to the invention in any way.

The catalytic treatment in the gas phase according to the invention is advantageously carried out at a temperature of between 225 and 325° C. and, preferably, under a pressure between atmospheric pressure and 1.5 MPa.

The contact time can vary between 5 and 100 seconds, but a contact time of between 25 and 75 seconds is preferred.

As mentioned above, the HF/F134a molar ratio can vary between 0.05 and 0.5. However, it is preferred to operate with a HF/F134a molar ratio of between 0.125 and 0.200 and, more particularly, a molar ratio close to that corresponding to the HF/F134a azeotrope (0.15).

At the conclusion of the treatment according to the invention, the gas flow no longer contains, or only contains traces of, olefinic impurities and can then be subjected to the conventional operations (separation, distillation, washing with water, neutralisation, and the like) in order to separate unconverted HF and saturated compounds other than F134a.

The fluorination catalysts to be used for the implementation of the process according to the invention can be mass catalysts or supported catalysts, the support which is stable in the reaction medium being, for example, an active charcoal, aluminium fluoride or aluminium phosphate.

Among the mass catalysts, there may be mentioned more particularly chromium oxide prepared according to any one of the methods known to those skilled in the art (sol/gel process, precipitation of the hydroxide from chromium salts, reduction of chromic anhydride, and the like). Derivatives of metals such as nickel, iron, manganese or cobalt may also be suitable, alone or in combination with chromium, in the form of bulk catalysts but also in the form of supported catalysts.

Supported catalysts can be used in the form of balls, extrudates, pellets or even, if the operation is carried out in a stationary bed, in the form of fragments. For bulk catalysts, the pellet or ball form is generally preferred. When the operation is carried out in a fluid bed, it is preferred to use a catalyst in the form of balls or extrudates.

As non-limiting examples of catalysts, there may be mentioned:
  microbeads of chromium oxide obtained by the sol/gel process as described in the patent FR 2,501,062,
  catalysts of chromium oxide deposited on active charcoal (U.S. Pat. No. 4,474,895), on aluminium phosphate (patent EP 55,958) or on aluminium fluoride (U.S. Pat. Nos. 4,579,974 and 4,579,976),
  mixed catalysts of chromium oxide and nickel fluoride deposited on aluminium fluoride (patent application EP 0,486,333).

The abovementioned patents, the contents of which are incorporated here by reference, broadly describe the method of preparing these catalysts, but also their method of activation, that is to say of prior conversion of the catalyst to stable active species by fluorination using gaseous HF diluted by inert compounds (nitrogen) or non-inert compounds (air or 1,1,2-trichloro-1,2,2-trifluoroethane). During this activation, the metal oxides which serve as active material (for example chromium oxide) or as support (for example alumina) can be partially or completely converted to the corresponding fluorides.

The following examples illustrate the invention without limiting it.

Example 1

50 ml of a catalyst consisting of microbeads of mass chromium oxide, prepared as described in Example 3 of the patent FR 2,501,062, are placed in a tubular reactor made of Inconel 600 with an internal diameter of 28 mm and a volume of 200 ml. This catalytic reactor, operating as a stationary bed, is then fed with a mixture, in the gas state, consisting of crude F134a and HF in proportions such that the HF/F134a molar ratio is equal to 0.25.

The crude F134a has the following composition by weight:
  F134a: 97%
  F1122: 0.08%
  F133a: 0.45%
  F125+F143a: 2%

The temperature of the reactor is fixed at 225° C. and its absolute pressure at 1.5 MPa. The feed flow rate (d) of the crude F134a+HF mixture varies so that the contact time (t) moves between 11 and 55 seconds, d and t being connected by the relationship:

$$t = \frac{15 \times 3600 \times V \times 273}{22.4 \times d \times (T + 273)}$$

where
  t=contact time in seconds
  d=flow rate in moles/hour
  V=bulk catalyst volume, expressed in liters
  T=temperature of the reactor in degrees Celsius A gaseous sample, freed from excess HF, is analysed by vapor phase chromatography at the reactor outlet in order to follow the development of the F1122 level in the organic products. The removal yield (R) of the F1122 is defined by the relationship:

$$R(\text{in \%}) = 100 \times \frac{Ci - Cf}{Ci}$$

where Ci is the initial concentration of F1122 in the organic reactants fed to the reactor and Cf the final concentration of F1122 in the organic products at the reactor outlet, these concentrations being expressed in volume per million (vpm).

The following Table I collates the results obtained on the same catalytic charge as a function of the contact time and the age of the catalyst.

TABLE I

| | OPERATING CONDITIONS | | | RESULTS | |
|---|---|---|---|---|---|
| TEST No. | Contact time (sec) | Duration of test (hours) | Age of catalyst (hours)* | Cf (vpm) | R (%) |
| 1-A | 22 | 5 | 16.5 | <20 | >97.6 |
| 1-B | 30 | 5 | 21.5 | <5 | >99.4 |
| 1-C | 52 | 5 | 26.5 | <5 | >99.4 |
| 1-D | 12 | 3 | 29.5 | approx. 80 | >88.9 |
| 1-E | 32 | 24 | 53.5 | <5 | >99.3 |
| 1-F | 30 | 2 | 55.5 | <10 | >98.6 |

TABLE I-continued

| | OPERATING CONDITIONS | | | RESULTS | |
|---|---|---|---|---|---|
| TEST No. | Contact time (sec) | Duration of test (hours) | Age of catalyst (hours)* | Cf (vpm) | R (%) |
| 1-G | 30 | 30 | 83.5 | <10 | >98.6 |
| 1-H | 30 | 71 | 124.5 | <15 | >97.8 |
| 1-I(**) | 29 | 6 | 130.5 | <5 | >99.3 |
| 1-J(**) | 11 | 3 | 133.5 | approx. 30 | >96 |

*at the end of the test
(**)tests carried out at 250° C.

Examination of these results shows that, at 225° C., a virtually complete removal of F1122 is obtained with a contact time of approximately 30 seconds and that the removal yield of F1122 is still reasonable when the cumulative age of the catalyst reaches 124.5 hours (tests 1-E to 1-H).

An increase in the temperature from 225 to 250° C. (tests 1-I and 1-J), on the same catalyst charge, again gives a virtually complete degree of removal for a contact time of approximately 30 seconds (test 1-I). For a contact time of 11 seconds (test 1-J), the removal yield falls to 96%.

Example 2

100 ml of a catalyst based on nickel fluoride and chromium oxide deposited on aluminium fluoride are introduced into the same reactor as in Example 1. The physicochemical characteristics of this catalyst, prepared as described in the patent application EP 0,486,333 and activated in a stationary bed by a nitrogen/HF mixture, are the following:

| Chemical composition (by weight): | |
|---|---|
| fluorine | 58.6% |
| aluminium | 25.9% |
| nickel | 6.4% |
| chromium | 6.0% |

| Physical properties: | |
|---|---|
| apparent density (in bulk) | 0.85 g/cm$^3$ |
| BET surface | 23 m$^2$/g |
| volume of the pores with a radius of between 40Å and 63 μm | 0.4 cm$^3$/g |
| surface of the pores with a radius greater than 40Å | 23 m$^2$/g |

After a final "in situ" activation of the catalyst using a gaseous HF/F133a (molar ratio: 0.4) mixture between 25 and 250° C., the reactor is fed with a gaseous mixture consisting of HF and crude F134a in proportions such that the HF/F134a molar ratio is equal to 0.18, that is to say close to the azeotropic composition.

The crude F134a used has the following molar composition:

| | |
|---|---|
| F134a | 95.9% |
| F1122 | 0.24% |
| F133a | 3.8% |
| F125 | 0.02% |
| F143a | 0.04% |

By working under an absolute pressure of 1.0 MPa, with a contact time of approximately 50 seconds and at different temperatures (250, 300 and 350° C.), the results collated in the following Table II were obtained.

TABLE II

| | OPERATING CONDITIONS | | | | RESULTS | |
|---|---|---|---|---|---|---|
| TEST No. | Temperature (° C.) | Contact time (sec) | Duration of test (h) | Age of catalyst (h)* | Cf (vpm) | R (%) |
| 2-A | 250 | 50.8 | 6 | 6 | <5 | 99.8 |
| 2-B | " | 45.3 | 18 | 24 | <5 | 99.8 |
| 2-C | 300 | 50.7 | 7 | 31 | <5 | 99.8 |
| 2-D | " | 50.0 | 13.5 | 44.5 | <5 | 99.8 |
| 2-E | " | 52.1 | 9.5 | 54 | <5 | 99.8 |
| 2-F | " | 50.4 | 17.5 | 71.5 | <5 | 99.8 |
| 2-G | 350 | 54.2 | 8 | 79.5 | 11 | 99.5 |
| 2-H | " | 47.8 | 15 | 94.5 | 13 | 99.4 |
| 2-I | 250 | 52.4 | 7.5 | 102 | <5 | 99.8 |
| 2-J | " | 50.8 | 19 | 121 | <5 | 99.8 |

*at the end of the test

The results obtained are very impressive, even at high temperature on the same catalyst charge. Tests 2-I and 2-J entirely confirm the activity of the catalyst and its resistance to temperature changes.

Example 3

A tubular reactor is used which is made of Inconel 600 with an internal diameter of 38 mm and a useful volume of 400 ml, and in which are placed 200 ml of a commercial catalyst of bulk chromium oxide in the form of 4.8×4.8 mm pellets, activated beforehand in a stationary bed using a nitrogen/HF mixture.

The physicochemical characteristics of this catalyst, after activation, are the following:

| Chemical composition (by weight): | |
|---|---|
| fluorine | 20.0 % |
| chromium | 56.3 % |
| carbon | 3.5 % |
| oxygen | 20.2 % |

| Physical properties: | |
|---|---|
| apparent density (in bulk) | 1.21 g/cm$^3$ |
| BET surface | 124 m$^2$/g |
| volume of the pores with a radius of between 40Å and 63 μm | 0.14 cm$^3$/g |
| surface of the pores with a radius greater than 40Å | 42.3 m$^2$/g |

After a final "in situ" activation of the catalyst at 350° C. under atmospheric pressure using a gaseous HP/F133a (molar ratio: 4) mixture and with a contact time of 4 seconds, the reactor is fed with a gaseous mixture consisting of HF and crude F134a in proportions such that the HF/F134a molar ratio is equal to 0.18, that is to say close to the azeotropic composition.

The crude F134a used has the following molar composition:

| | |
|---|---:|
| F134a | 95.6% |
| F1122 | 0.19% |
| F133a | 3.0% |
| F125 | 0.05% |
| F143a | 0.05% |

By working under an absolute pressure of 1.0 MPa, with a contact time varying between 25 and 100 seconds and at different temperatures (225 and 250° C., then 200° C. and again 225° C.), the results collated in the following Table III were obtained.

TABLE III

| | OPERATING CONDITIONS | | | | RESULTS | |
|---|---|---|---|---|---|---|
| TEST No. | Temperature (° C.) | Contact time (sec) | Duration of test (h) | Age of catalyst (h)* | Cf (vpm) | R (%) |
| 3-A | 225 | 49.5 | 5.5 | 5.5 | <5 | >99.9 |
| " | " | " | 16.5 | 22 | " | " |
| " | " | " | 5.5 | 27.5 | " | " |
| 3-B | 250 | 49.8 | 5.1 | 32.6 | <5 | >99.9 |
| " | " | " | 16.4 | 49 | " | " |
| " | " | " | 2 | 51 | " | " |
| 3-C | 250 | 97.5 | 6.25 | 57.25 | <5 | >99.9 |
| " | " | " | 16.75 | 74 | " | " |
| 3-D | 200 | 50.4 | 5 | 79 | 60 | 96.8 |
| " | " | " | 18 | 97 | 130 | 93.1 |
| 3-E | 200 | 26.4 | 8 | 105 | 400 | 78.7 |
| " | " | " | 17 | 122 | 425 | 77.3 |
| 3-F | 225 | 49.0 | 23 | 145 | 30 | 98.4 |

*at the end of the test

Examination of the results shows that a temperature of 200° C., especially with a contact time of approximately 26 seconds (tests 3-D and 3-E), does not give a virtually complete removal of F1122.

The control test 3-F, again carried out at 225° C. and with a contact time of 49 seconds, gives 30 vpm of unconverted F1122 (in place of less than 5 vpm for test 3-A), which shows a slight fall in activity of the catalyst after 145 hours of continuous operation.

Example 4

100 ml of a catalyst of chromium on active charcoal (3 mm) are introduced into the same reactor as in Example 1. The physico-chemical characteristics of said catalyst, after activation, are as follows:

| | |
|---|---|
| chromium content | 20.3% by weight |
| fluorine content | 13.6% by weight |
| BET surface | 204 m²/g |
| surface of the pores with a radius greater than 40 Å | 15.4 m²/g |
| volume of the pores with a radius of between 40Å and 63 μm | 0.43 cm³/g |

This catalytic reactor, operating as a stationary bed, is then fed with a gaseous mixture having the following molar composition:

| | |
|---|---|
| F134a | 81.9% |
| F1122 | 0.11% |
| F133a | 2.6% |
| HF | 15.4% | and operation is carried out at 250° C. under an absolute pressure of 1 MPa with a contact time of approximately 70 seconds.

By working under these operating conditions, the concentration (Cf) of F1122 in the organic products at the reactor outlet is less than 2 vpm; that corresponds to a removal yield of at least 99.9%. These performances are quite stable; they were obtained for 740 hours of operation.

What is claimed is:

1. Process for the purification of a crude 1,1,1,2-tetrafluoroethane (F134a) containing unsaturated olefinic impurities comprising treating a gaseous mixture of crude 1,1,1,2-tetrafluoroethane and hydrofluoric acid (HF) in the gas phase, in the absence of hydrochloric acid, at a temperature of between 225 and 325° C., a contact time between 25 and 75 seconds and under a pressure ranging from atmospheric pressure to 2.5 MPa, in the presence of a fluorination catalyst, the HF/F134a molar ratio being between 0.05 and 0.5.

2. Process according to claim 1, wherein the contact time is between 5 and 100 seconds.

3. Process according to claim 1, wherein the HF/F134a molar ration is between 0.125 and 0.200.

4. Process according to claim 1, wherein the fluorination catalyst is a bulk or supported catalyst based on chromium, nickel, iron, manganese and/or cobalt.

5. Process according to claim 4, wherein the catalyst is chromium oxide in the form of microbeads or supported on active charcoal, aluminium phosphate or aluminium fluoride, or a mixture of chromium oxide and nickel fluoride deposited on a support of aluminium fluoride.

6. The process of claim 1 wherein said crude F134a is made by a gas phase catalytic fluorination of 1-chloro-2,2,2-trifluoroethane (F133a) which also produces (1) 1-chloro-2,2-difluoroethylene (F1122) as a by-product of a dehydrofluorination side reaction and (2) hydrochloric acid as a result of the reversible main reaction of F133a and HF producing F134a and hydrochloric acid, and wherein the absence of hydrochloric acid avoids the retrogradation of F134a to F133a.

7. Process for the purification of a crude 1,1,1,2-tetrafluoroethane (F134a) containing unsaturated olefinic impurities including 1-chloro-2,2-difluoroethylene (F1122), said crude F134a being made by a reversible main reaction of a gas phase catalytic fluorination of 1-chloro-2,2,2-trifluoroethane (F133a) with hydrofluoric acid (HF) which produces (a) hydrochloric acid as a result of the reversible main reaction of F133a and HF producing F134a and hydrochloric acid, and which also produces (b) said F1122 as a by-product of a dehydrofluorination side reaction, said process comprising:
  treating a gaseous mixture consisting of said crude F134a and hydrofluoric acid in the gas phase, in the absence of said hydrochloric acid, at a temperature of between 225 and 325° C., a contact time between 25 and 75 seconds and under a pressure ranging from atmospheric pressure to 2.5 MPa, in the presence of a fluorination catalyst, and the HF/F134a molar ratio being between 0.05 and 0.5; and
  wherein the treating converts said unsaturated olefinic impurities to saturated compounds for separation by distillation.

8. The process of claim 7 wherein said gas mixture contains not greater than trace amounts of the olefinic impurities after the treating.

9. A method for the purification of crude 1,1,1,2-tetrafluoroethane produced by reacting trichloroethylene with hydrogen fluoride, comprising bringing low hydrogen chloride content 1,1,1,2-tetrafluoroethane containing unsaturated impurities and having a concentration of hydrogen chloride of not higher than 2 mol %, and hydrogen fluoride in an amount at least equimolar to the unsaturated impurities, into contact with a fluorination catalyst in a vapor phase, so as to decrease the content of the unsaturated impurities, and comprising bringing the low hydrogen chloride content 1,1,1,2-tetrafluoroethane containing hydrogen fluoride into contact with the fluorination catalyst without further addition of hydrogen fluoride.

10. A method according to claim 9, wherein the low hydrogen chloride content 1,1,1,2-tetrafluoroethane contains 1,1,1,2-tetrafluoroethane in an amount of not less than 70 mol %.

11. A method according to claim 9 wherein the low hydrogen chloride content 1,1,1,2-tetrafluoroethane contains 1,1,1,2-tetrafluoro-2-chloroethane in an amount of not more than 10 mol %.

12. A method according to claim 9, wherein the catalyst comprises at least one metal selected from the group consisting of Mg, Cr, Fe, Co and Ni.

13. A method according to claim 9, wherein the contact of the low hydrogen chloride content 1,1,1,2-tetrafluoroethane with the catalyst is carried out at a temperature of 130° to 280° C. or 225° to 325° C.

14. The process of claim 1 wherein said crude 1,1,1,2-tetrafluoroethane is produced by reacting trichloroethylene with hydrogen fluoride.

15. A method for the purification of crude 1,1,1,2-tetrafluoroethane comprising bringing low hydrogen chloride content 1,1,1,2-tetrafluoroethane containing unsaturated impurities and being without hydrogen chloride or having a concentration of hydrogen chloride of not higher than 2 mol %, and hydrogen fluoride at least in an amount to convert said unsaturated impurities to saturated compounds or in an amount at least equimolar to the unsaturated impurities, into contact with a fluorination catalyst in a vapor phase, so as to decrease the content of the unsaturated impurities or so that the 1,1,1,2-tetrafluoroethane contains no or only traces of said unsaturated impurities, and comprising bringing the low hydrogen chloride content 1,1,1,2-tetrafluoroethane containing hydrogen fluoride into contact with the fluorination catalyst without further addition of hydrogen fluoride.

16. The process of claim 1 wherein the gaseous mixture of said crude F134a and hydrofluoric acid is treated in the gas phase in the presence of the fluorination catalyst under a pressure ranging from atmospheric pressure to 1.5 MPa, and the HF/F134a molar ratio is between 0.125 and 0.200.

17. The process of claim 1 wherein the crude 1,1,1,2-tetrafluoroethane contains up to 7% F133a $CF_3CH_2Cl$.

* * * * *